United States Patent [19]

Danos et al.

[11] Patent Number: 5,955,331

[45] Date of Patent: *Sep. 21, 1999

[54] RECOMBINANT RETROVIRUSES WITH AMPHOTROPIC AND ECOTROPIC HOST RANGES

[75] Inventors: Olivier Danos, Somerville; Richard C. Mulligan, Cambridge, both of Mass.

[73] Assignee: Whitehead Institute for Biomedical Research, Cambridge, Mass.

[ * ] Notice: This patent is subject to a terminal disclaimer.

[21] Appl. No.: 08/488,421

[22] Filed: Jun. 7, 1995

Related U.S. Application Data

[63] Continuation of application No. 08/198,649, Feb. 22, 1994, Pat. No. 5,449,614, which is a continuation of application No. 07/869,047, Apr. 14, 1992, abandoned, which is a continuation of application No. 07/239,545, Sep. 1, 1988, abandoned.

[51] Int. Cl.$^6$ .............................. C12N 5/10; C12N 15/48; C12N 7/00
[52] U.S. Cl. .................................... 435/172.3; 435/235.1; 435/325; 536/23.72
[58] Field of Search ............................ 435/172.3, 240.1, 435/240.2, 235.1, 325; 935/57, 70; 536/23.72

[56] References Cited

U.S. PATENT DOCUMENTS

| | | | |
|---|---|---|---|
| 4,650,764 | 3/1987 | Temin et al. | 435/350 |
| 5,278,056 | 1/1994 | Bank et al. | 435/456 |
| 5,449,614 | 9/1995 | Danos et al. | 435/172.3 |

FOREIGN PATENT DOCUMENTS

| | | |
|---|---|---|
| 3636287 A1 | 4/1988 | Germany . |
| WO 89/07136 | 8/1989 | WIPO . |
| WO 90/02806 | 3/1990 | WIPO . |

OTHER PUBLICATIONS

Danos and Mulligen, 1988, "Expression of retroviral transacting functions from complementary crippled genomes:a system for helper free packaging of retroviral vectors," *J. Cellular Biochemistry Supplement 12B*:Abstract H106 p. 172.

Josef Ban et al., 1989, "Bovine Leukaemia Virus Packaging Cell Line for Retrovirus–mediated Gene Transfer," *J. gen. Virol.* 70: 1987–1993.

Olivier Danos and Richard C. Mulligan, 1988, "Safe and efficient generation of recombinant retroviruses with amphotropic and ecotropic host ranges," *Proc. Natl. Acad. Sci. U.S.A. 85*: 6460–6464.

J. Sorge et al., 1984, "Amphotropic Retrovirus Vector System for Human Cell Gene Transfer" *Mol. and Cell. Biol.* 4:1730–1737.

R.D. Cone and R.C. Mulligan, 1984, "High–efficiency gene transfer into mammalian cells: Generation of helper–free recombinant retrovirus with broad mammalian host range" *Proc. Natl. Acad. Sci. U.S.A. 81*: 6349–6353.

R. Mann and D. Baltimore, 1985 *J. Virol 54*:401–407.

A.D. Miller and C. Buttimore, 1985, "Factors Involved in Productin of Helper Virus–free Retrovirus Vectors" *Somat. Cell Genet.*, 12:175–183.

A.D. Miller et al., 1986, "Redesign of Retrovirus Packaging Cell Lines to Avoid Recombination Leading to Helper Virus Production" *Mol. and Cell. Biol.* 6:2895–2902.

M.A. Bender et al., 1987, "Evidence that the Packaging Signal of Moloney Murine Leukemia Virus Extends in the gag Region" *J. Virol 61*:1639–1646.

R.A. Bosselmann et al., 1987, "Replication–Defective Chimeric Helper Provirus and Factors Affecting Generation of Competent Virus: Expression of Moloney Murine Leukemia Virus Structural Genes via the Metallothionein Promoter" *Mol. and Cell. Biol.* 7:1797–1806.

O. Danos and R.C. Mulligan, 1988, *UCLA Symposium*.

D. Markowitz et al., 1988, A Safe Packaging Line for Gene Transfer: Separating Viral Genes on Two Different Plasmids *J. Virol 62*:1120–1124.

O. Danos and R.C. Mulligan, 1988, *RNA Tumor Viruses, Cold Spring Harbor Sumpos.* May 17–22.

D. Markowitz et al., 1988, *Virology 167*:400–406.

S.K. Chattopadhyay et al., 1981, "Genomes of Murine Leukemia Viruses Isolated from Wild Mice," *J. Virology* 39:777–791.

R. Mann et al., 1985, "Construction of a Retrovirus Packaging Mutant and Its Use to Produce Helper–Free Defective Retrovirus" *Cell 33*:153–159.

S. Watanbe and H. Temin, 1983, "Construction of a Helper Cell Line for Avian Reticuloendotheliosis Virus Cloning Vectors" *Mol. and Cell. Biol.* 3:2241–2249.

Small, J. and G. Scangos et al., 1983, "Recombination During Gene Transfer into mouse Cells Can Restore the Function of deleted Genes," *Science 219*:174–176.

S.A. Rosenburg et al., 1990, *New Engl. J. Med. 323*:570–578.

Hurford, Jr. R. et al., 1995, "Gene therapy of metastatic cancer by in vivo retroviral gene targeting," *Nat. Genet.* 10(4):430–435.

Gilboa, E. "Retrovirus vectos and their uses in molecular biology," *Bioessays* 5(6):252–257 (1986).

Lim, B. et al. "Retrovirus–mediated gene transfer of human adenosine deaminase: expression of functional enzyme in murine hematopoietic stem cells in vivo," *Molec. Cell. Biol.* 7(10):3459–3465 (1987).

Wilson, J. et al. "Correction of the genetic defect in hepatocytes from the Watanabe heritable hyperlipidemic rabbit," *Proc. of the Natl. Acad. of Sci.* 85:4421–4425 (1988).

Israel et al. "Retroviral–mediated transfer and amplification of a functional human factor VIII gene," *Blood* 75(5):1074–1080 (1990).

Morgenstern et al. "Advanced mammalian gene transfer: high titre retroviral vectors with multiple drug selection markers and a complementary helper–free packaging cell line," *Nucleic Acids Research* 18(12):3587–3596 (1990).

*Primary Examiner*—George C. Elliott
*Assistant Examiner*—John S. Brusca
*Attorney, Agent, or Firm*—Hale & Dorr LLP

[57] ABSTRACT

Packaging cell lines useful for the generation of helper-free recombinant retroviruses with amphotropic or ecotropic host ranges, methods of constructing such packaging cell lines and methods of using the recombinant retroviruses to introduce DNA of interest into eukaryotic cells, both in vitro and in vivo.

17 Claims, 5 Drawing Sheets

RECOMBINANT RETROVIRUSES WITH AMPHOTROPIC AND ECOTROPIC HOST RANGES

This is a continuation of application Ser. No. 08/198,649, filed Feb. 22, 1994 U.S. Pat. No. 5,449,614, which is a continuation of application Ser. No. 07/869,047 filed Apr. 14, 1992, now abandoned, which is a continuation of application Ser. No. 07/239,545 filed Sep. 1, 1988 now abandoned.

DESCRIPTION

Funding

Work described herein was supported by grants from the National Institutes of Health and Fellowships from the Fondation pour la Recherche Medicale, the National Institutes of Health-Centre National de la Recherche Scientifique Program for Scientific Collaboration and the European Molecular Biology Organization.

Background

Since the late 1970s, there has been considerable progress made in developing methods by which DNA can be introduced into eukaryotic cells, especially mammalian cells. Two approaches widely used today are transient gene expression assays and stable transformation of cells. In the latter, DNA of interest is introduced stably into a host (eukaryotic) cell, generally by integrating the exogenous DNA into host cell chromosomal DNA. A particularly promising approach to stable transformation of cells makes use of recombinant retroviruses, which serve as vectors by which the DNA of interest is transferred into eukaryotic cells.

Retroviruses appear to be particularly well suited for DNA or gene transfer because of several important features of their life cycle. Mulligan, R. C., Chapter 8 In: Experimental Manipulation of Gene Expression, Academic Press, pp. 155–173 (1983); Coffin, J. In: RNA Tumor Viruses, Weiss, R. et al. (ed.), Cold Spring Harbor Laboratory, Vol. 2, pp. 36–38 (1985). For example, although the retroviral genome is RNA, a DNA intermediate is formed during the retroviral life cycle and is efficiently integrated into chromosomal DNA of infected cells. In addition, mammalian cells are not generally killed by productive infection by retroviruses. Further, retrovirus infection of many types of pluripotent and differentiated is possible, both in vitro and in vivo.

Considerable effort has been put into developing recombinant retroviruses useful for introducing DNA of interest into mammalian cells, in part because of their potential use in gene therapy and in production in eukaryotic host cells of proteins of interest.

Most often, the initial step in the generation of recombinant retrovirus for mammalian gene transfer studies is the introduction of a suitable proviral DNA vector into fibroblastic cells that produce the necessary viral proteins for encapsidation of the desired recombinant RNA. Since, for most gene transfer applications, the generation of pure stocks of recombinant virus free of replication-competent helper virus is desirable, there has been considerable interest in the development of cell lines that produce the necessary viral gene products for encapsidation, yet do not themselves yield detectable helper virus or transfer of viral genes. Coffin, J. In: RNA Tumor Viruses, Weiss, R. et al. (ed.), Cold Spring Harbor Laboratory, Vol. 2. pp. 36–73, (1985); Mann, R. et al., Cell 33:153–159 (1983); Watanabe, S. and H. M. Temin, Mol. Cell. Biol. 3:2241–2249 (1983); Cone, R. D. and R. C. Mulligan, Proc. Natl. Acad. Sci., USA, 81:6349–6353 (1984); Miller, A. D. and C. Buttimore, Mol. Cell. Biol., 6:2895–2902 (1986); Bosselmann, R. A. et al., Mol. Cell. Biol., 7:1797–1806 (1986). In the first generation of such "helper-free" packaging cell lines, expression of the necessary viral proteins was achieved through the stable introduction of a mutant Moloney murine leukemia virus (Mo-MuLV) proviral genome containing a 350-base-pair (bp) deletion of the Psi sequence, a sequence required for efficient encapsidation of the Mo-MuLV genome. Mann, R. et al., Cell, 33:153–159 (1983). The resulting cell line, termed Psi-2 has been successfully used by many investigators. An additional packaging cell line, Psi-AM, which has a further alteration, has been described and has also been widely used. Cone, R. D. and R. C. Mulligan, Proc. Natl. Acad. Sci., USA, 81:6349–6353 (1984). However, it has been shown that virus-producing cell lines derived from Psi-2 and Psi-AM produce low levels of virus containing the Psi$^-$ genome and, therefore, are able to transfer the mutant proviral genome to recipient cells, albeit at low efficiency. Miller, A. D. and C. Buttimore, Mol. Cell. Biol., 6:2895–2902 (1986).

In addition, in a minority of cases, the encapsidation of the Psi$^-$ genome appears to lead to the generation of wild-type virus through recombinational events involving a copackaged recombinant genome carrying the Psi sequence. Cone, R. D. and R. C. Mulligan, Proc. Natl. Acad. Sci., USA, 81:6349–6353 (1984); Miller, A. D. and C. Buttimore, Mol. Cell. Biol., 6:2895–2902 (1986); Bosselmann, R. A. et al., Mol. Cell. Biol., 7:1797–1806 (1987); Sorge, J. et al., Mol. Cell. Biol., 4:1730–1737 (1984); Miller, A. D. et al., Somat. Cell Mol. Genet., 12:175–183 (1986); Bender, M. A. et al., J. Virol., 61:1639–1646 (1987).

There have been numerous attempts to eliminate these problems, for example, by introducing additional alterations into the Psi$^-$ genome. Miller, A. D. and C. Buttimore, Mol. Cell. Biol., 6:2895–2902 (1986). In these latter packaging systems the chances of transferring the packaging functions or generating wild-type virus are significantly reduced; however, the possibility of the events occurring remains, since the additional mutations could still be corrected by recombinational events involving a Psi$^+$ vector genome. Indeed, the presence of helper virus has been reported in virus-producing cell lines derived from such a packaging cell. Bosselmann, R. A. et al., Mol. Cell. Biol., 7:1797–1806 (1987).

In U.S. Pat. No. 4,650,764, Temin and Watanabe describe a helper cell to be used to provide retrovirus protein required by a replication incompetent recombinant retrovirus in order to be able to replicate. They describe a host cell and two retrovirus gene sequences: one which has a helper portion which codes for a retrovirus protein and is capable of expressing that protein and a defective portion which generally codes for encapsidation and makes the gene sequence replication incompetent and a second which has a defective retrovirus portion (which normally codes for at least one retroviral protein), a portion encoding a foreign protein and a retrovirus cis portion.

There have also been reports of attempts to obtain stable packaging cell lines in which the retroviral functions were carried on different plasmids. Watanabe, S. and H. M. Temin, *Mol. Cell. Biol.*, 3:2241–2249 (1983); Bosselmann, R. A. et al., *Mol. Cell. Biol.*, 7:1797–1806 (1987). However, the cell lines described in those reports were either unstable or functioned poorly. Markowitz and co-workers describe construction of an ecotropic packaging cell line generated by using helper virus DNA in which the gag and pol genes were on one plasmid and the env gene on another. In each of these cases, the two complementary constructs were co-transfected, which can result in loss of most of the advantage of having physically separated the viral genes, since recombination between transfected plasmids before they integrate is known to happen at a high frequency. Small, J. and G. Scangos, *Science,* 219:174–176 (1983).

Although retroviruses have been shown to have properties which make them particularly well suited to serve as recombinant vectors by which DNA of interest can be introduced into eukaryotic cells and, thus, are of considerable interest as tools to be used in introducing such DNA into humans (e.g., for gene replacement or therapy), the fact that packaging functions can be transferred to recipient cells and/or wild-type virus can be generated could limit their acceptability for use in humans. It would be very valuable if recombinant retroviral vectors capable of introducing DNA of interest into eukaryotic cells but unable to transfer packaging functions or revert to wild-type virus were available.

DISCLOSURE OF THE INVENTION

The present invention relates to packaging cell lines useful for the generation of helper-free recombinant retroviruses with amphotropic or ecotropic host ranges, to construction of such cell lines and to methods of using the recombinant retroviruses to introduce DNA of interest into eukaryotic cells, particularly mammalian cells. The recombinant retroviruses are useful for the introduction of DNA of interest (all or a portion of a gene or genes encoding a product whose expression in a cell is desired) into eukaryotic cells, in which the encoded product is expressed. The recombinant retroviruses are useful for production of a protein of interest, either in vitro or in vivo. That is, they can be used to produce proteins in culture, for subsequent therapeutic or diagnostic use, or to provide a means by which defective cells can produce a protein otherwise produced in insufficient quantities or in abnormal/nonfunctional forms. The recombinant retroviruses are particularly useful for purposes such as gene therapy or gene replacement because they have been constructed in such a manner that they do not transfer the packaging functions or yield helper virus and, thus, are free of two key characteristics which limit the use of presently-available recombinant retroviruses for somatic gene transfer in large animals and human gene replacement therapies.

BRIEF DESCRIPTION OF THE DRAWINGS

FIG. 1 is a schematic representation of generation of helper virus by recombination in heterozygous virions. Three cases of co-packaged RNA genomes are presented. In these cases, the helper virus genome carrying the gag-pol and env genes and the defective recombinant, whose transduced insert is depicted as an open box, are presented. Solid and open boxes at the extremities represent the R-U5 and the U3-R terminal sequences. Shown at the left is the nature of the helper genome modification for each case. The open box at the 3' end represents the simian virus 40 (SV40) polyadenylation signals. Frameshift mutations are represented by an X. Shaded areas indicate homologous regions on the genomes, through which, if recombination occurs, helper virus can be formed. Transfer refers to transmission of the Psi⁻ genome to recipient cells. Helper formation refers to the generation of wild-type replication-competent virus.

DETAILED DESCRIPTION OF THE INVENTION

The present invention is a new set of packaging cell lines useful for the generation of virus with amphotropic or ecotropic host ranges. Such packaging cell lines have been constructed in such a manner that the problems encountered with presently-available cell lines—transfer of packaging functions and formation of helper virus—have been avoided. To eliminate these previously-encountered limitations, two mutant Moloney murine leukemia virus-derived proviral genomes carrying complementary mutations in the gag-pol or env regions were sequentially introduced into NIH 3T3 cells by DNA-mediated cotransformation. Both genomes contain a deletion of the Psi sequence necessary for the efficient encapsidation of retroviral genomes into virus particles and additional alterations at the 3' end of the provirus.

The resulting packaging cell lines, designated Psi CRIP and Psi CRE, have been shown to be useful to isolate clones that stably produce high titers ($10^6$ colony-forming units/ml) of recombinant retroviruses with amphotropic and ecotropic host ranges, respectively. In addition, viral producers derived from the packaging cell lines do not transfer the packaging functions, or yield helper virus. These properties of the Psi CRIP and Psi CRE packaging lines make them particularly valuable reagents for in vivo gene transfer studies aimed at cell lineage analysis and the development of human gene replacement therapies. Psi CRIP and Psi CRE have been deposited at the American Type Culture Collection, Rockville, Md., under accession numbers CRL/9808 and CRL/9807, respectively, under the terms of the Budapest Treaty.

As described briefly below and in detail in the Examples, retrovirus packaging cell lines have been produced by introducing complementary frameshift mutations into the retroviral genes which encode the packaging functions, in which the cis-acting alterations described are also present. Mann, R. et al., *Cell*, 33: 153–159 (1983); Miller, A. D. and C. Buttimore, *Mol. Cell. Biol.*, 6:2895–2902 (1986). As a result of the method used, it is essentially impossible for helper virus to be generated, as occurs with presently-available cell lines. That is, to eliminate the problems of transfer of packaging functions and helper virus formation encountered with other packaging systems, two mutant Moloney Murine Leukemia virus (Mo-MuLV)-derived proviral genomes, which carry complementary mutations in the gag, the pol or the env regions, were introduced sequentially into NIH 3T3 cells by cotransformation. Each proviral genome also included a deletion of the Psi sequence necessary for the efficient encapsidation of retroviral genomes into virus particles and additional alterations in the 3' end of the provirus.

Sequential introduction of the two complementary retroviral constructs expressing the packaging functions is an important feature of the method of the present invention and is the basis for (results in) essential elimination of the possibility that recombination between the two constructs can occur, either as a result of the cotransfection procedure or during gene conversion events between tandemly repeated structures cointegrated at the same chromosomal locus. The complementary frameshift mutations cannot be rescued upon recombination with the replication-defective vector genome and, thus, the generation of helper virus in the Psi CRIP and Psi CRE packaging lines requires a complex and unlikely chain of events. For generation of helper virus to occur, one of the mutated genomes would first have to regain a 3' LTR and a Psi sequence, by a double recombination with a vector genome, in order to be able, in a subsequent round of infection, to recombine with the complementary mutant genome and yield a wild-type genome. Alternatively, it is possible to imagine that a reversion of one of the mutations could occur, followed by a double-recombination event. The probability of these outcomes is extremely low and as described below, when a high-titer viral stock was pseudotyped several times, alternatively by using Psi CRIP or Psi CRE to increase the probability of observing a reverse transcriptase-mediated recombination event, no transmissible functional helper genome was generated. In a parallel experiment in which PA317 was used as the amphotropic packaging line, a recombinant was shown to result. Although its structure has not yet been studied, it appears that the recombinant was the product of at least one recombination event involving the retroviral vector and the Psi$^-$ genome, presumably within the 88-base segment they share at their 3' extremities (from the ClaI site at position 7674 to the Rsa I site at position 7762).

Figure 2:
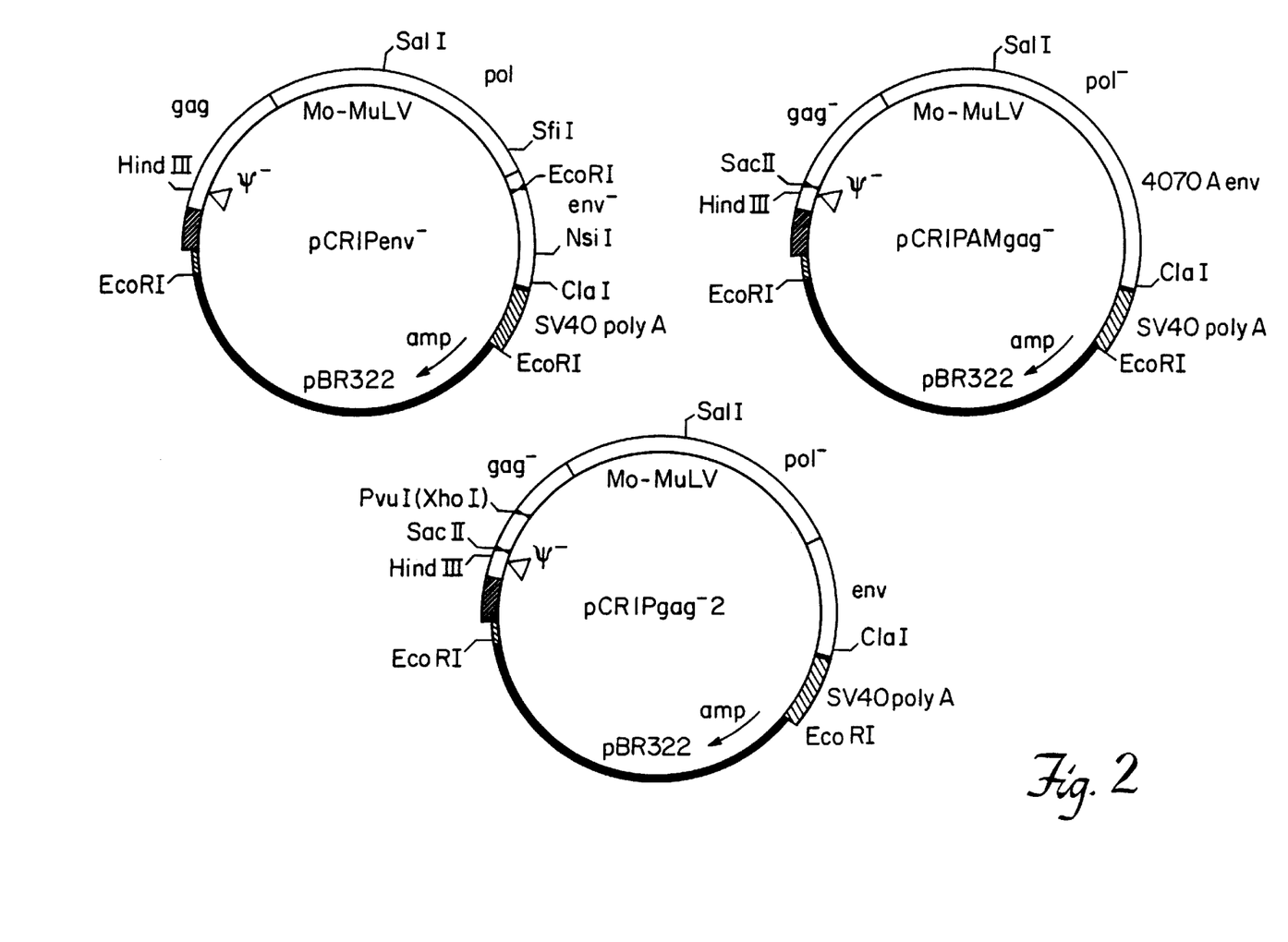
FIG. 2 shows the structure of the CRIP plasmids.
Figure 3:
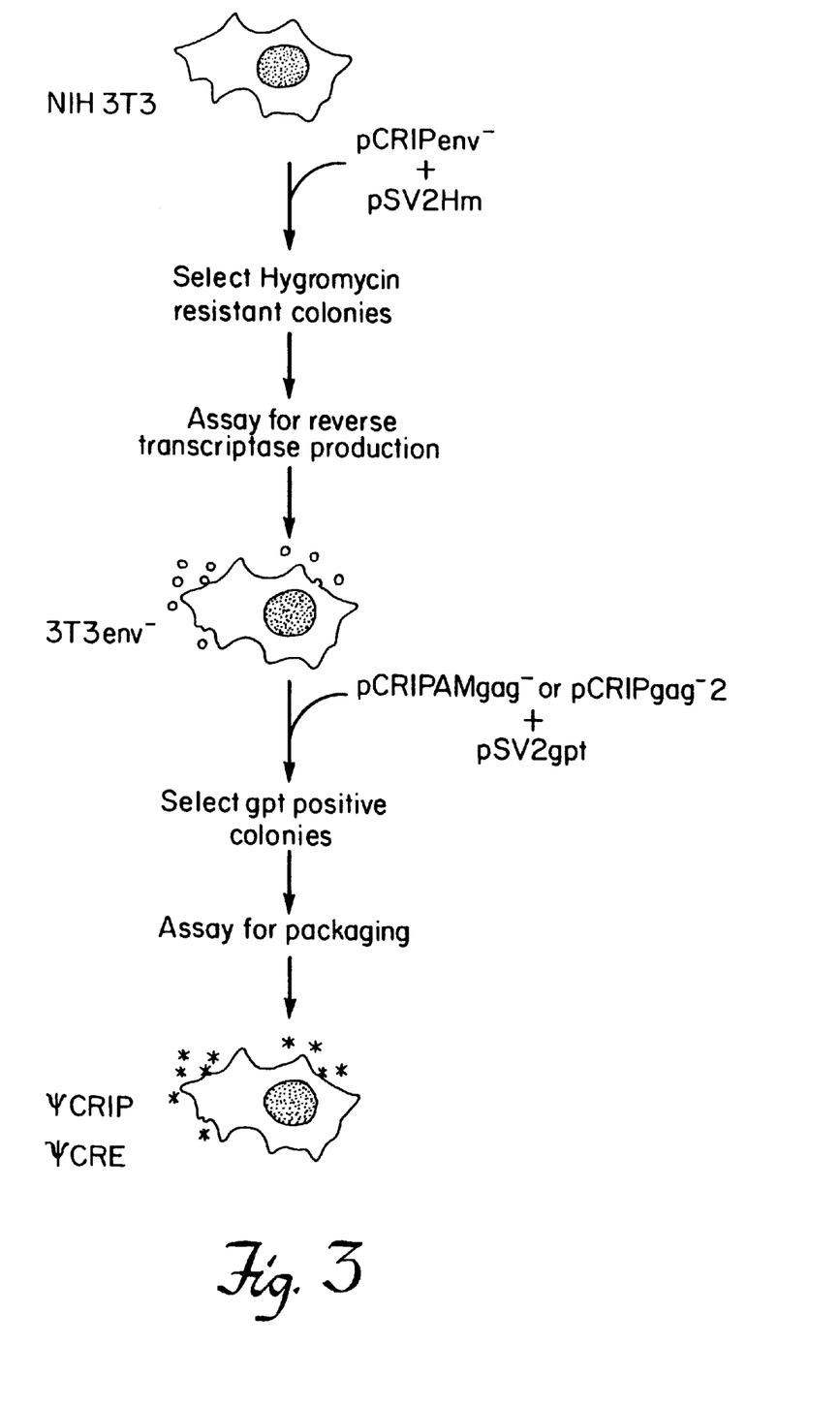
FIG. 3 is a schematic representation of the protocol used for isolation of Psi CRIP and Psi CRE packaging cell lines.

The strategy used in the method of the present invention is described briefly below, represented schematically in FIG. 3 and described in detail in Example 2. In the first round of transfection, one construct, designated pCRIP env$^-$ (see FIG. 2), was co-transfected with a plasmid, designated pSVHm, which confers resistance to hygromycin into NIH 3T3 cells by DNA-mediated co-transformation. Stable transformants were selected by culturing co-transfected cells in the presence of hygromycin B; only co-transfected cells survived. Clones were assayed for reverse transcriptase activity and two of the positive clones were selected. These two selected clones, which were env$^-$ cells, were subsequently used to produce the Psi CRIP and the Psi CRE packaging lines. In the second round of transfections, one of two constructs, designated pCRIPAMgag$^-$ and pCRIPgag$^{-2}$ (see FIG. 2), respectively, was introduced into the env$^-$ cells, along with a plasmid, designated pSV2gpt, which contains the bacterial xanthine-guanine phosphoribosyltransferase (gpt) gene as a dominant selectable marker. Transformants were selected by culturing co-transfected cells in guanine phosphoribosyltransferase-selective medium. The resulting colonies were assayed for their ability to package the BAG retroviral vector. Two clones, designated CRIP14 and CRE25 were selected as the amphotropic and the ecotropic packaging lines, respectively. This strategy—introduction of the constructs into the recipient cell line by using two independent rounds of transfections—made it possible to initially select clones expressing optimal levels of gag and pol proteins by measuring the levels of reverse transcriptase they released and then to test for the production of a functional envelope in secondary transfectants by using a packaging assay. This procedure also resulted in the generation of an env$^-$ cell line that may prove useful for the generation of viral pseudotypes containing retroviral gag proteins and other nonretroviral envelope proteins.

High-titer viral stocks can be routinely obtained with producer clones isolated from Psi CRIP or Psi CRE. For instance, after transfection of the packaging lines with the HSGneo vector, which includes the 5' portion of the gag sequences as well as the enhancer deletion, producer clones with titers of $10^6$ cfu/ml were isolated. This is equivalent to what can be achieved with Psi-2. Such titers are high enough to ensure infection of the minor pool of pluripotent stem cells present in bone marrow. Williams, D. A. et al., *Nature*, 310:476–480 (1984); Dick, J. E. et al., *Cell*, 42:71–79 (1985); Lemischka, I. R. et al., *Cell*, 45:917–927 (1986). Efficient transduction of murine hematopoietic stem cells with Psi CRIP and Psi CRE producers has been carried out.

High-titer viral producers have been derived from both Psi CRIP and Psi CRE with more than 15 constructs. Whenever tested in the his mobilization assay, the producers were negative for transfer of the packaging functions and, therefore, free of helper virus, even after carrying the cells in culture for a long period of time. For many gene transfer applications, the level of packaging function transfer and frequency of helper virus formation found with the previously developed cell lines may be inconsequential. However, the practical elimination of any transfer and/or recombination events potentially leading to the emergence of helper virus, as has been achieved by the method of the present invention, may be particularly valuable for studies of cell lineage and may prove to be extremely important in the establishment of safe and efficient conditions for somatic gene transfer in large animals and human gene replacement therapies.

Figure 1:
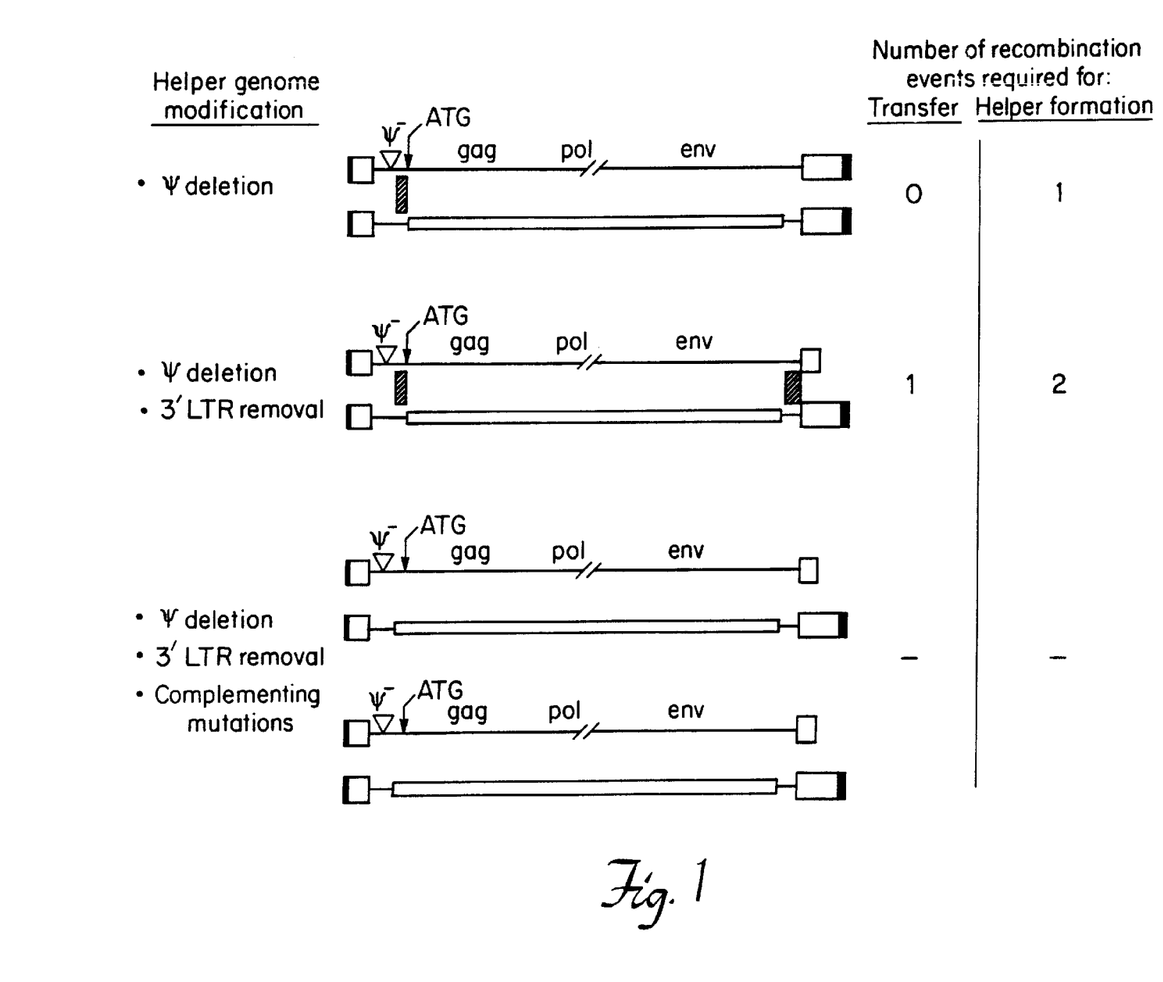

As described previously, the determining events in the transfer of viral genes and the generation of wild-type virus by existing packaging cell lines appear to be the inefficient, but detectable, encapsidation of Psi$^-$ genomes into virus particles, and subsequent recombination between copackaged Psi$^-$ genomes and Psi$^+$ vector genomes during the process of reverse transcription. As shown in FIG. 1, the Psi$^-$ genome utilized in the construction of Psi-2 and Psi-AM cells can be encapsidated into virus particles at low efficiency and transferred to recipient cells without any recombinational events (referred to as "transfer" in FIG. 1). Mann, R., and D. Baltimore, *J. Virol,* 54:401–407 (1985); Danos, O. et al., *Ciba Found. Symp.,* 120:68–77 (1985). Surprisingly, the generation of wild-type virus by Psi-2 derived cells (referred to as "helper formation" in FIG. 1) is not frequent, although the retention of specific viral sequences in the vector genome can increase the likelihood of obtaining wildtype virus through one recombinational event. Miller, A. D. and C. Buttimore, *Mol. Cell. Biol.,* 6:2895–2902 (1986); Miller, A. D. et al., *Somat. Cell Mol. Genet.,* 12:175–183 (1986); Bender, M. A. et al., *J. Virol.,* 61:1639–1646 (1987). Although the additional alterations in the 3' long terminal repeat (LTR) of $Psi^-$ genomes, employed in the generation of the PA317 cell line by Miller and Buttimore, would not be expected to affect the encapsidation of the resulting $Psi^-$ genomes, efficient transfer of the $Psi^-$ genomes to cells would require a recombinational event. Miller, A. D. and C. Buttimore, *Mol. Cell. Biol.,* 6:2895–2902 (1986); Goldfarb, M. P. and R. A. Weinberg, *J. Virol.,* 38:136–150 (1981). Accordingly, transfer of the viral genes to cells should be dramatically reduced in comparison to Psi-2 and Psi-AM cells. In addition, the generation of wild-type virus from such cells would require two recombinational events (FIG. 1).

In spite of the additional mutations in the proviral genomes used in the generation of PA317 cells, transfer of viral genes and the generation of wild-type virus in virus-producing cells derived from PA317 was detected. This has been detected by others as well. Bosselmann, R. A. et al., *Mol. Cell. Biol.,* 7:1797–1806 (1987). To further reduce the possibility of these events, the method of the present invention makes use of separate proviral genomes that contain deletions of the Psi sequences and 3' LTR and encode either the gag-pol gene or the env gene (FIG. 2). Rather than attempt to express the specific subgenomic coding sequences by using heterologous expression vectors, "genomic-like" structures were retained to ensure high levels of expression. Accordingly, well-characterized mutations in the gag-pol or env gene were transferred into $Psi^-$ constructs to generate $gag-pol^+$ $env^-$ and $gag-pol^-$ $env^+$ constructs. To generate packaging cell lines with ecotropic host range, proviral constructs containing the env gene from the Mo-MuLV genome were used. To generate cells with amphotropic host range, the env coding sequences from the 4070A virus genome were introduced in place of the Mo-MuLV-derived env sequences. Chattopadhyay, S. K. et al., *J. Virol.,* 39:777–791 (1981).

As described above, the resulting constructs, shown in FIG. 2, were then introduced sequentially into NIH 3T3 cells through two rounds of transfection and co-selection with different dominant-acting selectable markers (hygromycin, gpt). This protocol was chosen to optimize the stable expression of each construct and to prevent recombination between the complementary plasmid DNAs that might occur at the DNA level if they were co-transfected together. Small, J. and G. Scangos, *Science,* 219:174–176 (1983). As described herein, NIH 3T3 cells were transfected with the two constructs to produce packaging cell lines. However, other types of mammalian cells, particularly monkey and human cells, can be used to produce packaging lines.

Introduction of DNA of Interest Using Psi CRIP and Psi CRE

The packaging cell lines of the present invention can be used, both in vitro and in vivo, to introduce DNA of interest, which can be all or a portion of a gene encoding a protein or a polypeptide whose expression in a eukaryotic cell is desired, into such cells. For example, if production of a particular protein or polypeptide by eukaryotic cells (e.g., insulin, human growth hormone) is desired (e.g., to provide a means by which useful quantities of a protein or polypeptide to be administered for therapeutic purposes or used in a diagnostic context), either of the packaging cell lines can be used to introduce DNA encoding the desired product into the cells, using known techniques. For example, recombinant virus can be harvested from the producer cells and used as a viral stock to infect recipient cells, which are then selected on the basis of expression of the gene so introduced (e.g., in the case of insulin, selection can be carried out using an appropriate antibody). Alternatively, the gene of interest can be introduced into cells in culture by co-cultivating the cells and the producer (packaging) cells. The two types of cells are subsequently separated, using known techniques, and the infected cells recovered. After introduction of the gene in this manner, cells are maintained under conditions appropriate for their survival and expression of the encoded product, which is removed from the cultured cells by known techniques.

The packaging cell lines of the present invention can also be used to introduce DNA of interest into mammalian cells, such as human cells, which will subsequently be applied to the body (e.g., by grafting or transplantation), where they will produce the desired protein or polypeptide on an ongoing basis. For example, they can be used to modify keratinocytes, endothelial cells, fibroblasts or hepatocytes, which will subsequently produce the encoded protein or polypeptide on an ongoing basis. Such modifications can be carried out, for example, in keratinocytes by the method described in U.S. Pat. No. 4,868,116; in fibroblasts by the method described in U.S. application Ser. No. 07/152,749; in endothelial cells by the method described in U.S. application Ser. No. 07/096,074; or in hepatocytes by the method described in U.S. application Ser. No. 07/131,926. The teachings of these four co-pending patent applications are incorporated herein by reference.

The present invention will now be illustrated by the following examples, which are not intended to be limiting in any way.

EXAMPLE 1

Construction of CRIP Plasmids

In the work described in this and the following example, the following methods and materials were used, as appropriate:

Cell Lines and Plasmids Used

NIH 3T3 cells were obtained from G. Cooper (Dana-Farber Cancer Institute) and grown in Dulbecco's modified Eagle's medium (DMEM) containing 10% (vol/vol) calf serum. Drug-resistance selections in transfected or infected NIH 3T3 cells were done in the following concentrations of compounds: G418 (GIBCO) at 1 mg/ml, hygromycin (Calibiochem) at 0.2 mg/ml, and histidinol (Sigma) at 0.5 mM.

T lymphoma cells (mouse BW 5147 and human Jurkat) were grown in RPMI medium containing 10% fetal calf serum and 50 uM beta-mercaptoethanol (complete RPMI).

Plasmids pA5 and pR21, containing mutated Mo-MuLV proviral sequences, were kindly provided by S. Goff (Columbia University). Colicelli, J. et al., *Mol. Gen. Genet.*, 199:536–539 (1985). The mutant pA5 carries an 8-bp Sac II linker inserted at position 623 of the Mo-MuLV genome and pR21 has two 10-bp EcoRI linkers at position 5987. The cloned 4070A amphotropic genome pL1 was obtained from A. Oliff (Merck), and pSV2Hm was from P. Berg (Stanford University). All plasmids were grown in *Escherichia coli* (*E. coli*) MC1061.

Nucleic Acids Procedures and Enzymatic Assays

DNA constructions, isolation of genomic DNA, and blot analysis were performed by standard procedures. Maniatis, T. et al., *Molecular Cloning: A Laboratory Manual*, (Cold Spring Harbor Lab., Cold Spring Harbor, N.Y.), (1982). High-specific-activity $^{32}$P-labeled DNA probes were synthesized by using the random-priming method. Feinberg, A. P. et al., *Anal. Biochem.*, 132:6–13 (1983). The method of Goff et al., was used to assay for the presence of reverse transcriptase activity in the culture medium of exponentially growing cells. Goff, S. et al., *J. Virol.*, 38:239–248 (1981). Staining the beta-galactosidase activity in intact cells was done according to Sanes, J. R. et al., *EMBO J.*, 5:3133–3142 (1986).

Transfections, Infections, and Determination of Viral Titers

Transfection of calcium phosphate/DNA coprecipitates and infection of NIH 3T3 were done as described by Gorman et al. and Cone et al., respectively. Gorman, S. et al., *Science*, 221:551–553 (1983); Cone, R. D. et al., *Mol. Cell. Biol.*, 7:887–897 (1987).

For the determination of viral titers, producers were grown to subconfluence (5×10$^6$ cells on a 10-cm dish). 10 ml of fresh medium was added, and virus was harvested 16 hr later. Viral stocks were filtered through a 0.45 um membrane and 2 ml of a dilution was applied to 5×10$^5$ NIH 3T3 cells on a 10-cm dish for 2.5 hr. The infected cells were grown for 48 hr. At this point, cells were lysed and their DNA was prepared for Southern blot analysis. Maniatis, T. et al., *Molecular Cloning: A Laboratory Manual*, (Cold Spring Harbor Laboratory, Cold Spring Harbor, N.Y.) (1982). When the retroviral vector contained a selectable marker, infected cells were split at a ratio of 1:10 in selective medium. The number of resistant colonies obtained, divided by two, was the titer in colony-forming units (cfu)/ml of the diluted stock used for the infection.

Mobilization Assay for the Production of Helper Virus and the Transfer of Packaging Functions The test cell line 116 was isolated after infection of NIH 3T3 by a recombinant retrovirus carrying the hisD selectable marker. The cell line contains a single copy of the replication defective provirus. Cells to be tested were grown to subconfluence and fresh medium was added. After 16 hours, medium was harvested and filtered through a 0.45 um filter. Two milliliters of this medium was applied to a dish containing 5×10$^5$ 116 cells. After 48 hours, the 116 cells were split at a ratio of 1:20 and allowed to grow for another 48 hours. At that time, the culture medium was changed and virus was harvested 16 hours later. The presence of hisD virus released by the 116 cells was then assayed by applying 2 ml of filtered culture medium to NIH 3T3. Infected cells were selected in medium lacking histidine but containing 0.5 mM histidinol.

Structure of the CRIP Plasmids

A parental plasmid, pCRIP (data not shown), was first constructed by replacing most of the 3' LTR in the pMOVPsi$^-$ by the SV40 early polyadenylation region. For this, the Cla I-EcoRI fragment of pMOVPsi$^-$ encompassing the 3' end of the env gene, the 3' LTR, and mouse cellular sequences was replaced by two fragments: a Cla I-Sal I fragment taken from pZipNeoSVX (enh$^-$) that contained a Sal I linker at the original Pvu II site (position 7934) and a Hpa I-EcoRI fragment from the SV40 genome (positions 2666–1782) with a Xho I linker at its Hpa I extremity. The pCRIPenv$^-$ plasmid, which is represented in FIG. 2, was obtained by exchanging the Sfi I-Nsi I fragment (positions 5382–7054) with the equivalent segment from the env mutant genome pR21. Colicelli, J. et al., *Mol. Gen. Genet.*, 199:537–539 (1985). To obtain pCRIPAMgag$^-$, also represented in FIG. 2, a fragment from Pst I (position 563, Hind III linkered) to Sal I (position 3705) of the gag-pol$^-$ mutant pA5 was ligated, in a pCRIP backbone, to the Sal I-Cla I fragment of the 4070A amphotropic Mo-MuLV cloned genome. Chattopadhyay, S. K. et al., *J. Virol.*, 39:777–791 (1981). The pCRIPgag$^-$2 plasmid, represented in FIG. 2, contained the same Pst I-Sal I fragment from pA5 introduced in the pCRIP backbone. The ecotropic envelope gene was kept and a second mutation in the gag sequences was introduced by cutting with Xho I (position 1560), filling in the extremities with the Klenow fragment of *E. coli* DNA polymerase I and religating. Mutations in the coding sequences are shown as X.

EXAMPLE 2

Isolation of Packaging Cell Lines

The starting material for all of the construction shown in FIG. 2 was the pMOV Psi$^-$ DNA. Mann, R. et al., *Cell*, 33:153–159 (1983). In each construction, a majority of the 3' LTR was removed and replaced with a DNA segment containing the SV40 early polyadenylylation site (see Example 1 for the precise boundaries of the constructions). The pCRIPenv-plasmid DNA was generated by exchanging a fragment spanning the 5' half of the env gene with the homologous fragment from an in vitro-generated mutant of Mo-MuLV containing two EcoRI linkers inserted in tandem (20-bp insert) at position 5987 of the Mo-MuLV genome. Colicelli, J. et al., *Mol. Gen. Genet.*, 199:537–539 (1985). In pCRIPAMgag$^-$, the region surrounding the start of the gag-pol gene was replaced by a homologous fragment from the mutant pA5, which contains an 8-bp Sac II linker at position 623 after the initiation codon for gag translation. In addition, the Sal I-Cla I fragment spanning the 3' end of the pol gene and most of the env gene were replaced by the corresponding fragment from the cloned 4070A amphotropic virus genome. Chattopadhyay, S. K. et al., *J. Virol*, 39:777–791 (1981). The third construction, pCRIPgag⁻2 contains the same basic structure as the pCRIPAMgag⁻, except that the ecotropic env sequences were retained and an additional mutation at the Xho I site at position 1560 was introduced (see Example 1). This latter mutation was designed to further prevent the possibility of recombinational events that could lead to the emergence of helper virus.

Pairs of complementary constructs (pCRIPenv⁻ and pCRIPAMgag⁻ or pCRIPenv⁻ and pCRIPgag⁻2) were sequentially introduced into NIH 3T3 cells by DNA-mediated co-transformation. Perucho, M. et al., *Cell*, 22:309–317 (1980); Robin, S. D. et al., *Cell*, 23:29–39 (1981). In the first round of transfection, the pCRIPenv⁻ plasmid was cotransfected with the plasmid pSVHm, which confers resistance to hygromycin B. Bernard, H. U. et al., *Exp. Cell Res.*, 158:237–243 (1985). Stable transformants were selected in the presence of hygromycin B (200 ug/ml). Sixteen clones were isolated and individually grown, and the presence of reverse transcriptase activity in the culture medium was assayed. The parental NIH 3T3 line was used as a negative control in the assay and positive controls included Psi-2 and Psi-AM cells. Thirteen clones were found to release reverse transcriptase activity, among which 9 showned 20 significantly higher levels (data not shown). Two of these positive clones ($env^{-1}$ and $env^{-15}$) were subsequently used: $env^{-1}$ was initially chosen to derive the amphotropic Psi CRIP packaging line as described below, and $env^{-15}$ was later selected as the parental clone for the ecotropic Psi CRE line, since it showed a 2-fold higher level of Mo-MuLV specific transcripts in an RNA gel blot analysis (data not shown).

In the second series of transfections, either the pCRIP-AMgag⁻ or the pCRIPgag⁻² plasmid was introduced into the env⁻ cells, along with the plasmid pSV2gpt, which contains the bacterial xanthine-guanine phosphoribosyltransferase gene as a dominant selectable marker. Mulligan, R. C. and Berg, P., *Proc. Natl. Acad. Sci. USA.*, 78:2072–2076 (1981). Clones isolated in guanine phosphoribosyltransferase-selective medium were expanded and tested for their ability to package the BAG retroviral vector (FIG. 3; Price, J. et al., *Proc. Natl. Acad. Sci., USA*, 84:156–160 (1987)) particles. For this analysis, each clone to be tested was infected by a helper-free stock of BAG virus (ecotropic for the CRIP clones and amphotropic for the CRE clones), and populations of 50–100 G418-resistant colonies were derived from each infection and grown in mass cultures. Price, J. et al., *Proc. Natl. Acad. Sci. USA*, 84:156–160 (1987). Virus production from each population was then checked by using culture supernatant to transfer G418-resistance and B-galacotosidase activity to NIH 3T3 cells. The packaging capacity, as measured by G418 or B-galactosidase titer of produce populations, varied within a 100-fold range (data not shown). As a control, NIH 3T3 or the $env^{-15}$ cells were shown to be negative in the packaging assay. Clone CRIP14 was selected as having the highest packaging capacity; when compared to Psi-AM and PA317 in the same assay, its packaging activity was shown to be 3.5-fold higher and equivalent, respectively. Clone CRE25 was chosen as the ecotropic packaging line and it was observed to be less active by a factor of 3–5 than Psi-2 cells.

Producer Clones Derived from Psi CRIP and Psi CRE

The titering of populations of BAG virus-producing cells served to select the best packaging clones but was not an accurate estimation of their performance. To obtain more quantitative data about the titers that could be generated with the Psi CRIP and the Psi CRE lines, the two cell linese were stably transfected with the vector HSGneo (see FIG. 3). This retroviral vector has the following features: 1) it contains the Mo-MuLV splice donor and a portion of the gag sequences which have been shown to significantly increase titer; 2) the neo gene is driven by an internal promoter (human histone H4); and 3) the enhancer sequences have been deleted from the 3' LTR.

Colonies were selected in the presence of G418, individually picked, and expanded. Supernatant from these cultures (16 producers for each of the packaging lines) was used to transfer G418 resistance to NIH 3T3 cells. Titers of the best producers were found to be $1.3 \times 10^6$ cfu/ml and $0.7 \times 10^6$ cfu/ml for Psi CRIP and Psi CRE, respectively. The best Psi-2 producer tested in parallel had a titer of $1.7 \times 10^6$ cfu/ml. The amphotropic host range of the Psi CRIP-derived viruses was shown by the ability of the viruses to efficiently infect a wide range of mammalian cells of human, dog, rat, rabbit, and monkey origin.

Figure 4:
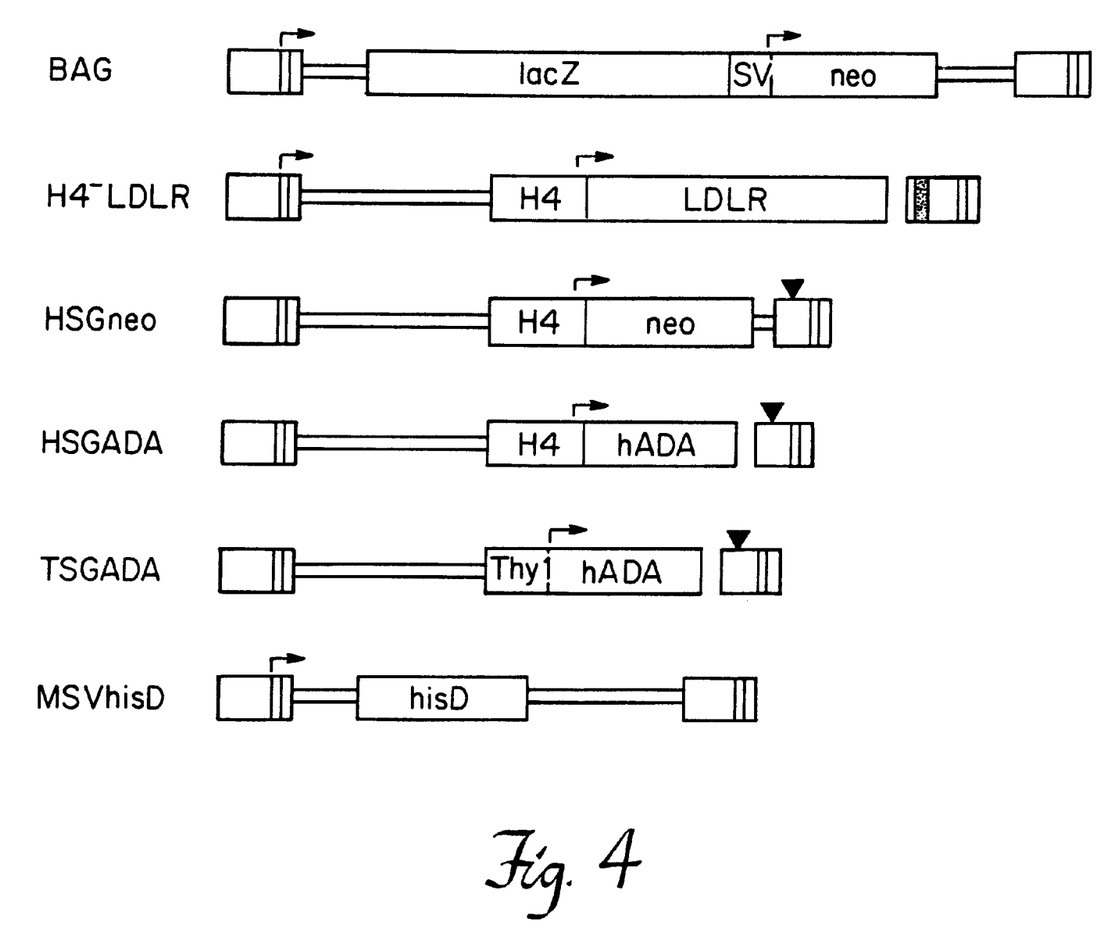
FIG. 4 shows the retroviral vectors used.
Figure 5:
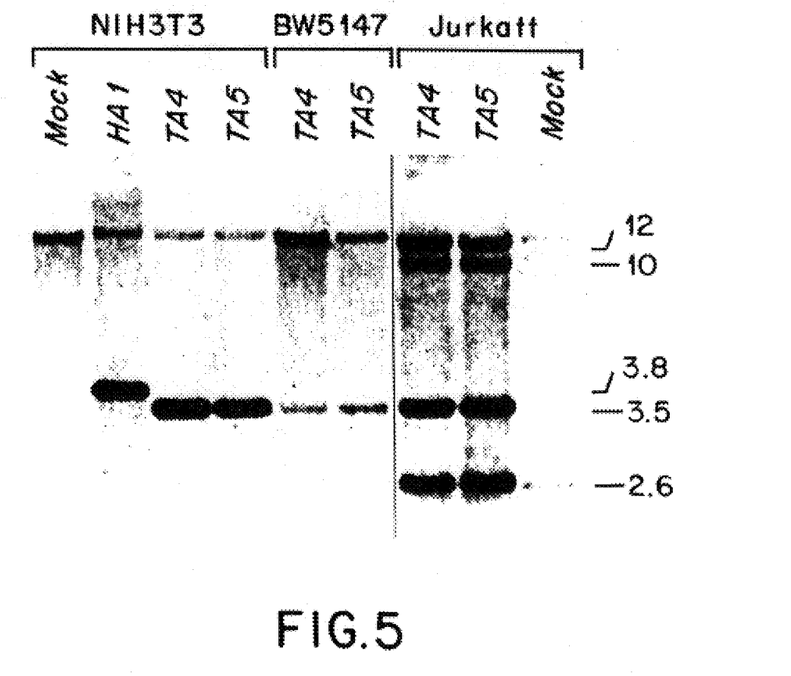
FIG. 5 shows the amphotropic host range of human ADA-transducing vectors produced with the Psi CRIP packaging line.

To demonstrate the amphotropic host range of virus generated from Psi CRIP cells, Psi CRIP clones producing recombinant viruses designed to transfer and express the human Adenosine Deaminase (ADA) cDNA were used. Orkin, S. H. et al., *Mol. Cell. Biol.*, 5:762–764 (1985). Two constructs, with the same basic design as HGSGneo, carrying the ADA cDNA under the control of different promoters (human histone H4, or murine Thy-1.2; see FIG. 4) were transfected into Psi CRIP cells along with pSv2neo. Southern, P. J. and P. Berg, *J. Mol. Appl. Genet.*, 1:327–341 (1982). Clones resistant to G418 were picked, individually grown and tested for transfer of the human ADA cDNA sequences. Cell lines, including NIH 3T3 and, in the case of the TSGADA producers, T cell lymphomas of murine (BW5147) or human (Jurkat) origin were infected and after two days, genomic DNA was prepared. Samples of DNA were digested with Kpn I, which cuts once in the recombinant proviruses LTR and the digestion products were analyzed on a Southern blot, using the human cDNA as a probe. The result of such an analysis is shown in FIG. 5. The transfer of the exogenous ADA sequences by the HSGADA or the TSGADA recombinant viruses was demonstrated by the appearance in the DNA of infected cells of a new 3.8 kb or 3.5 kb band, respectively. Although infectibility of the BW5147 cells was poor, close to 100% of the human cells could be infected by co-cultivation with the Psi CRIP producers, since the exogenous 3.5 kb band from the ADA provirus is at least as intense as the three endogenous 12.0 kb, 10.0 kb and 2.6 kb bands.

Characterization of the Packaging Lines for Transfer of Packaging Functions, Helper-Virus Formation, and Stability A mobilization assay was used to determine the extent to which recombinant virus generated from Psi CRIP- or Psi CRE-derived cells lines was helper-free. The mobilization assay is one in which the cell line 116, containing a single copy of the MSVhisD recombinant provirus, is challenged by a supernatant from virus-producing cell lines or infected cells and subsequently tested for release of the recombinant virus it harbors. Infection of the 116 cell line with culture supernatants harvested from Psi-2 cells or from Psi-2-derived producer cells led to the recovery of $2\times10^3$ his cfu/ml. Since these Psi-2 and Psi-2 producer cell lines remained negative in assays for replication-competent virus, the mobilization assay was likely detecting transfer of the Psi$^-$ genome. Culture supernatants from Psi CRIP, Psi CRE, PA317 (Miller, A. D. and C. Buttimore, *Mol. Cell. Biol.*, 6:2895–2902 (1986)), and all producer clones tested were not able to mobilize the MSVhisD provirus (data not shown).

Figure 6:
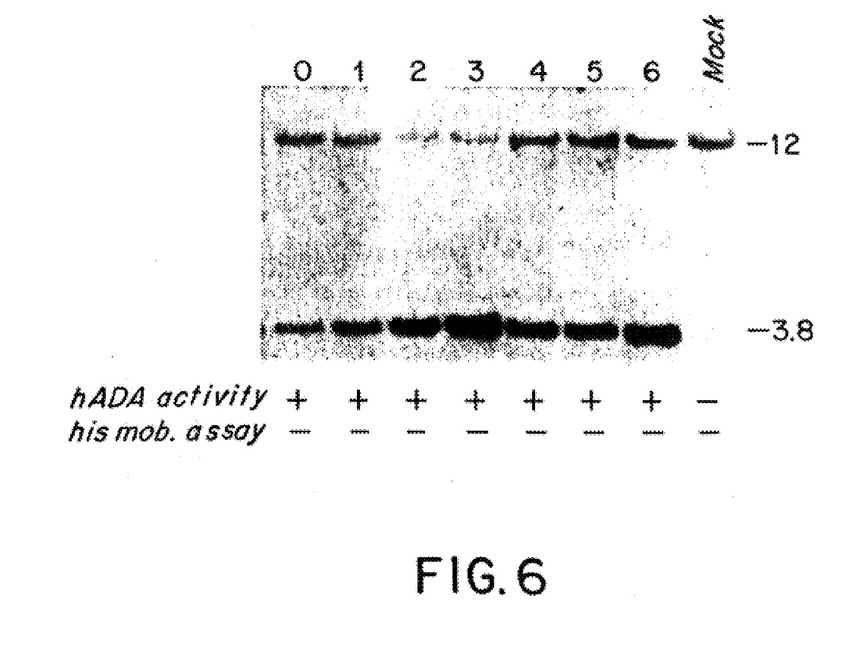
FIG. 6 shows the stability of the Psi CRIP HA1 producer clone.

The stability of virus production was also examined and the appearance of helper virus upon long-term cultivation of Psi CRIP- and Psi CRE-derived clones producing recombinant retrovirus determined. Cells were split at a ratio of 1:20 and grown for 3 days (3 or 4 doublings), at which point the culture medium was changed and virus was harvested 16 hr later. After this harvest, cells were split and the same cycle was repeated six times. Each collected culture supernatant was tested in this mobilization assay and used to infect NIH 3T3 as described above. None of these virus stocks was able to transfer the packaging functions. Each population of infected NIH 3T3 cells contained a comparable number of copies of integrated recombinant provirus as revealed by Southern blot analysis. (See FIG. 6). No decrease in the viral titer or rearrangement of the transferred DNA was detected. A variety of other virus-producing cell lines have been tested in this way and yielded the same result.

Unfortunately, the propagation of the virus-producing cell line in culture, even for long periods of time, may not reveal the generation of wild-type virus, since the envelope protein expressed on the surface of the cells would prevent their efficient infection with wild-type virus released from a rare virus-producing cell. To maximize the likelihood of observing recombination events due to reverse transcriptase-mediated recombination between packaging genomes and vector genomes, the following experiment was designed. A retroviral vector containing the 5' gag sequences and the human low density lipoprotein receptor gene under the control of the H4 promoter (H4-LDLR, FIG. 3) was shuttled several times between amphotropic and ecotropic packaging lines and the appearance of helper virus was monitored in each infected cell population, by using the his mobilization assay. Initially, two amphotropic viral stocks of equivalent titers, harvested from either a Psi CRIP or a PA317 clone producing H4-LDLR and negative in the his assay were used. Two milliliters of each stock were then used to infect $5\times10^5$ Psi CRE cells. A supernatant was collected 48 hr after infection, and Psi CRIP or PA317 were infected again. The same cycle was repeated several times and seven viral stocks produced in each series of cross-infections (Psi CRIP/Psi CRE or PA317/Psi CRE) were tested for their ability to mobilize the MSVhisD provirus (Table 1). In two separate experiments, all stocks from the Psi CRIP/Psi CRE series were negative. On the other hand, when PA317 was employed as the amphotropic packaging line, transfer of the packaging functions became apparent after the fifth (experiment 1) and fourth (experiment 2) round of infection. The amphotropic nature of the virus mobilized from the 116 cells with the viral stocks of the PA317/Psi CRE series was demonstrated by showing that the virus efficiently infected CV1 (monkey) and the env$^-$15 cells, yet did not infect Psi CRIP cells. The structure of the amphotropic proviral genome has not been characterized, but it appears that the virus recovered from experiment 1 may be defective, since it does not spread, whereas the virus recombinant from experiment 2 is replication competent.

TABLE 1

Titers of culture supernatant from 116 cells infected by serial H4-LDLR viral stock

| | Titer, cfu/ml | | | |
|---|---|---|---|---|
| Viral Stock | PsiCRIP/PsiCRE | | PA317/PsiCRE | |
| Shuttle No. | Exp. 1 | Exp. 2 | Exp. 1 | Exp. 2 |
| 1 (ampho) | 0 | 0 | 0 | 0 |
| 2 (eco) | 0 | 0 | 0 | 0 |
| 3 (ampho) | 0 | 0 | 0 | 0 |
| 4 (eco) | 0 | 0 | 0 | 0 |
| 5 (ampho) | 0 | 0 | 0 | 0 |
| 6 (eco) | 0 | 0 | 325 | $5 \times 10^4$ |
| 7 (ampho) | 0 | 0 | 475 | $5 \times 10^4$ | ampho, Amphotropic; eco, ecotropic

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

We claim:

1. A stable retroviral packaging cell line which generates helper-free recombinant retrovirus with an amphotropic host range, said stable retroviral packaging cell line comprising packaging cells, wherein the retrovirally derived component of said packaging cells' genome comprises stably incorporated first and second replication-defective retroviral constructs, wherein said first and second replication-defective retroviral constructs:

1) encode and express mutually exclusive regions of the gag, pol, and env genes;
   2) were separately and sequentially introduced into the genome of said packaging cells; and
   wherein the incorporated env gene is derived from an amphotropic virus.

2. A stable retroviral packaging cell line according to claim 1 wherein:

a) the genome of the first replication-defective retroviral construct comprises:
   1) a defective Psi packaging region;
   2) a functional form of at least one of the group consisting of gag and pol;
   3) a defective env region; and b) the genome of the second replication-defective retroviral construct comprises:

1) a defective Psi packaging region;
2) a functional amphotropic env gene; and
3) defective gag and/or pol regions which corresponds to the gag and/or pol regions which are not defective in the first retroviral construct,
   wherein said sequential introduction into the genome of said packaging cells results in the expression of complete but physically separated gag, pol and env coding regions.

3. A packaging cell line according to claim 2 wherein said first and second replication-defective retroviral constructs additionally comprise 3' LTR sequences, and wherein there is a deletion in the 3' LTR sequence of said first or second retroviral construct.

4. A packaging cell line according to claim 2 wherein said first and second replication-defective retroviral constructs additionally comprise 3' LTR sequences, and wherein there are deletions in the 3' LTR sequences of said first and second replication-defective retroviral constructs.

5. A packaging cell line according to claim 3 or 4 wherein said deletions remove the entire 3' LTR sequence.

6. A packaging cell line according to claim 3 or 4 wherein the first replication-defective retroviral construct is pCRIPenv.

7. A packaging cell line according to claim 3 or 4 wherein the second replication-defective retroviral construct is pCRIPAMgag.

8. A method of using the packaging cell line according to any one of claims 1, 2, 3, or 4, comprising the step of producing amphotropic retrovirus in said cell line.

9. A method of using the packaging cell line of claim 5 comprising the step of producing amphotropic retrovirus in said cell line.

10. A method of using the packaging cell line of claim 6 comprising the step of producing amphotropic retrovirus in said cell line.

11. A method of using the packaging cell line of claim 7 comprising the step of producing amphotropic retrovirus in said cell line.

12. A method of making a stable retroviral packaging cell line which generates helper-free recombinant retrovirus with an amphotropic host range, comprising the steps of:

a) transfecting mammalian host cells with a first replication-defective retroviral construct, the genome of which comprises:
  i) sequences derived from the 5' and 3' LTRs of a first retrovirus of interest;
  (ii) a defective Psi packaging region;
  (iii) a functional form of at least one region selected from the group consisting of gag and pol;
  (iv) a defective env region; and
  (v) a eucaryotic promoter for expressing the functional retroviral genes;
b) culturing the transfected cells of step a);
c) transfecting the cells cultured in step b) with a second replication-defective retroviral construct, the genome of which comprises:
  (i) sequences derived from the 5' and 3' LTRs of a second retrovirus of interest;
  (ii) a defective Psi packaging region;
  (iii) a functional amphotropic env gene;
  (iv) defective gag and/or pol regions which corresponds to the gag and/or pol regions which are not defective in the first retroviral construct; and
d) culturing the cells transfected in step c) whereby a packaging cell comprising complete but physically separated gag/pol and env coding regions is produced.

13. A method according to claim 12 wherein said first and second replication-defective retroviral constructs additionally comprise 3' LTR sequences, and wherein there is a deletion in the 3' LTR sequence of said first or second replication-defective retroviral constructs.

14. A method according to claim 12 wherein said fist and second replication-defective retroviral constructs additionally comprise 3' LTR sequences, and wherein there are deletions in the 3' LTR sequences of said first and second replication-defective retroviral constructs.

15. A method according to claim 12 or 14 wherein said deletions remove the entire 3' LTR sequence.

16. A method according to claim 13 or 14 wherein the first replication-defective retroviral construct is pCRIPenv.

17. A method according to claim 13 or 14 wherein the second replication-defective retroviral construct is pCRIPAMgag.

* * * * *

UNITED STATES PATENT AND TRADEMARK OFFICE
CERTIFICATE OF CORRECTION

PATENT NO. : 5,955,331

DATED : September 21, 1999

INVENTOR(S) : Danos et al.

It is certified that error appears in the above-identified patent and that said Letters Patent is hereby corrected as shown below:

In claim 14, line 31, after "said," "fist" should be changed to --first--.

In claim 15, line 36, after "claim," "12" should be changed to --13--.

Signed and Sealed this

Eighth Day of February, 2000

Attest:

Q. TODD DICKINSON

*Attesting Officer*          *Commissioner of Patents and Trademarks*